(12) United States Patent
Ott et al.

(10) Patent No.: US 7,455,653 B2
(45) Date of Patent: Nov. 25, 2008

(54) METHOD AND APPARATUS FOR TREATING GAS FOR USE IN ENDOSCOPIC SURGERY

(75) Inventors: Douglas E. Ott, Macon, GA (US); John F. Schaefer, Macon, GA (US); Robert I. Gray, Macon, GA (US)

(73) Assignee: Lexion Medical, LLC, St. Paul, MN (US)

( * ) Notice: Subject to any disclaimer, the term of this patent is extended or adjusted under 35 U.S.C. 154(b) by 79 days.

(21) Appl. No.: 11/253,196

(22) Filed: Oct. 18, 2005

(65) Prior Publication Data

US 2006/0052742 A1 Mar. 9, 2006

Related U.S. Application Data

(60) Continuation of application No. 09/497,620, filed on Feb. 3, 2000, now Pat. No. 7,066,902, which is a division of application No. 09/081,186, filed on May 19, 1998, now Pat. No. 6,068,609.

(51) Int. Cl.
*A61M 37/00* (2006.01)

(52) U.S. Cl. ............................ 604/26; 604/23; 604/24; 261/129; 261/142; 236/44 R

(58) Field of Classification Search ............. 604/23–24, 604/26; 236/44; 261/129, 142; 128/203.14, 128/203.17, 203.27, 203.12

See application file for complete search history.

(56) References Cited

U.S. PATENT DOCUMENTS

| 4,621,632 | A | * | 11/1986 | Bartels et al. | ........... 128/203.27 |
| 5,411,474 | A | * | 5/1995 | Ott et al. | ........................ 604/26 |
| 6,039,696 | A | * | 3/2000 | Bell | ........................... 600/532 |
| 7,066,902 | B1 | * | 6/2006 | Ott et al. | ....................... 604/23 |

* cited by examiner

*Primary Examiner*—Manuel A Mendez
(74) *Attorney, Agent, or Firm*—Marshall & Melhorn, LLC

(57) ABSTRACT

An apparatus for conditioning gas for use in a medical procedure, such as endoscopy, the gas being received into the apparatus from a gas source. The apparatus comprises a housing defining a chamber having an entry port and an exit port. A humidification means comprising at least one water-retainer layer is disposed within the chamber in the path of travel of the gas for humidifying the gas as it passes through the chamber. A humidity sensor is disposed within the chamber that senses the humidity of the gas exiting the chamber. A monitoring circuit is connected to the humidity sensor that detects when the chamber requires a recharge of liquid based on the humidity of the gas in the chamber, and generates a recharge signal indicative thereof. A charging port on the housing provides access into the chamber to recharge the chamber with water. A heating element and temperature sensor are also disposed within the chamber. A control circuit further regulates the temperature of the gas exiting the chamber.

24 Claims, 4 Drawing Sheets

METHOD AND APPARATUS FOR TREATING GAS FOR USE IN ENDOSCOPIC SURGERY

CROSS REFERENCE TO RELATED APPLICATIONS

This is a continuation of application Ser. No. 09/497,620; filed Feb. 3, 2000, now U.S. Pat. No. 7,066,902 which is a divisional application of Ser. No. 09/081,186; filed May 19, 1998 now U.S. Pat. No. 6,068,609. The priority of application Ser. Nos. 09/497,620 and 09/081,186 are specifically claimed, and they are incorporated herein by reference, in their entireties. Application Ser. No. 09/497,620; filed Feb. 3, 2000, is pending as of the filing date of the present application.

BACKGROUND OF THE INVENTION

1. Field of Invention

This invention relates to conditioning gases used to inflate body cavities prior to and during medical procedures. More specifically, it relates to a compact device for, and method of, heating, humidifying and filtering insulation and other gases.

2. Description of the Related Art

From the beginning of laparoscopic surgical procedures some thirty years ago, it has been assumed that the condition of gases used to inflate body cavities and spaces were physiologically and pathologically benign. While the importance and use of temperature and moisture conditioning of anesthesia gases has been well known, until recently little attention had been given to the particulate, temperature and/or humidity condition of insufflation gases used to create a pneumoperitoneum. Reduction in core body temperature, introduction of foreign bodies and drying of surfaces (including peritoneal surfaces), resulting from the introduction of insufflation gases in such surgical procedures are continuing problems.

A commonly used insufflation gas is carbon dioxide which is typically provided as a liquid in compressed gas cylinders. The pressure in these cylinders, when at equilibrium with ambient environment of 20° C., is 57 atmospheres (5740 kPa). The carbon dioxide gas is typically provided to the surgical site at a pressure of 15 mmHg via an adjustable, throttling pressure regulator and flow controller called an insufflator. Many models of insufflators are available such as the Storz Model 26012 (Karl Storz Endoscopy-America Inc., Culver City, Calif.). In general, Insufflators do not filter, few have the capability to control the gas temperature, and none are known to have the capability of humidifying the gas.

It is known to filter insufflation gas to prevent inorganic particles such as metallic fillings or particles, rust, dust, and polymer particles from passing into the pneumoperitoneum (see, e.g., Ott, D. E., *J. Gynecol. Surg.*, 5:205-208 (1989)). The location and type of filter, however, are very important factors which will influence the effectiveness of the method. Filters having a pore size as small as 0.2 microns have been used in previous insufflation systems. These devices, however, utilize a filter material that is typically hydrophilic and when it becomes moist, loses its strength and some of its filtering effectiveness. Moreover, because these prior art filter devices are not hydrophobic, they lose their filtering capability by tearing under the water pressure caused by accidentally suctioning or siphoning peritoneal or irrigation fluids.

In addition, in order to compensate for the cool temperature and dryness of the carbon dioxide insufflation gas, an apparatus and method have been developed to control the temperature and humidity of the insufflation gas as it is delivered into the body. Such an apparatus and method are disclosed in commonly assigned U.S. Pat. No. 5,411,474 to Ott, et al., the entirety of which is herein incorporated by reference. Nevertheless, there is room for improvement of a heating, hydrating and filtering apparatus for the delivery of insufflation gases.

SUMMARY OF THE INVENTION

The present invention is directed to an apparatus and method for providing heated and humidified gas to a patient such that heat loss in transfer of the gas is minimized, and such that humidity of the gas is monitored and the temperature of the gas is controlled throughout the procedure.

Briefly, the present invention is directed to an apparatus for conditioning gas for use in a medical procedure, such as endoscopy, the gas being received into the apparatus from a gas source, such as an insufflator. The apparatus comprises a heater/hydrator having a housing that defines a chamber in which a humidification means and a heating means are disposed in the flow path of the gas through the chamber. The humidification means comprises at least one liquid-retainer layer capable of absorbing a liquid, such as water, supplied into the chamber for humidifying the gas as it travels through the chamber. The heating means comprises a heating element disposed in the chamber preferably between the liquid-retaining layers. A humidity sensor is provided in the chamber that senses the humidity of the gas in the chamber and a temperature sensor is provided in the chamber to detect the temperature of the gas. A charging port on the housing provides access into the chamber to recharge the chamber with liquid. A monitoring circuit is connected to the humidity sensor that monitors the humidity of the gas exiting the chamber and particularly detects when the chamber requires a recharge of liquid based on the humidity of the gas in the chamber, and generates a recharge signal indicative thereof. An audible and/or visual alarm device may be activated in response to the recharge signal. A control circuit controls electrical power supplied to the heating element to regulate the temperature of the gas exiting the chamber.

Moreover, the present invention relates to a method of providing, for any selected period of time, heated and humidified gas into a patient for a medical procedure comprising the steps of directing a gas from a gas source into a chamber; humidifying the gas within the chamber with a volume of liquid; sensing the humidity of the gas as it exits the chamber; and monitoring the humidity of the gas exiting the chamber. The gas from the gas source may be pressure and/or volumetrically controlled.

The above and other objects and advantages of the present invention will become more readily apparent when reference is made to the following description taken in conjunction with the accompanying drawings.

DETAILED DESCRIPTION OF THE PREFERRED EMBODIMENTS

The present invention is directed to a method and apparatus for heating and hydrating gas, wherein the humidity of the gas is monitored and the user is informed when the humidity of the gas exiting the apparatus drops below a predetermined threshold. The method and apparatus further provides a means to "recharge" the heater/hydrator with liquid, allowing use of the apparatus for an indefinite period of time. Thus, the apparatus can be used for any endoscopic or other procedure, regardless of its length and regardless of unexpected time delays during the procedure.

As used in the claims, "a" can mean one or more.

As used herein, "a predetermined temperature" is one that has been preset and is not altered during a procedure. For laparoscopic procedures, the desirable predetermined temperature is typically physiological body temperature, i.e., approximately 35 to 45° C.

As used herein, the term "liquid" means water (preferably sterile) or a combination of water and other substances, such as drugs or anesthetics, or a gel substance containing water and other substances.

As used herein, any apparatus "immediately adjacent" to a patient or an object indicates a position sufficiently physically close in proximity to the patient or object such that gas at a temperature in the apparatus will not lose more than 2° C. while traveling from the apparatus to the interior of the patient or object. Such a distance would be, for example, from about 0 to 10 inches, preferably from 0 to 10 cm, and more preferably from 0 to 3 cm.

Figure 1:
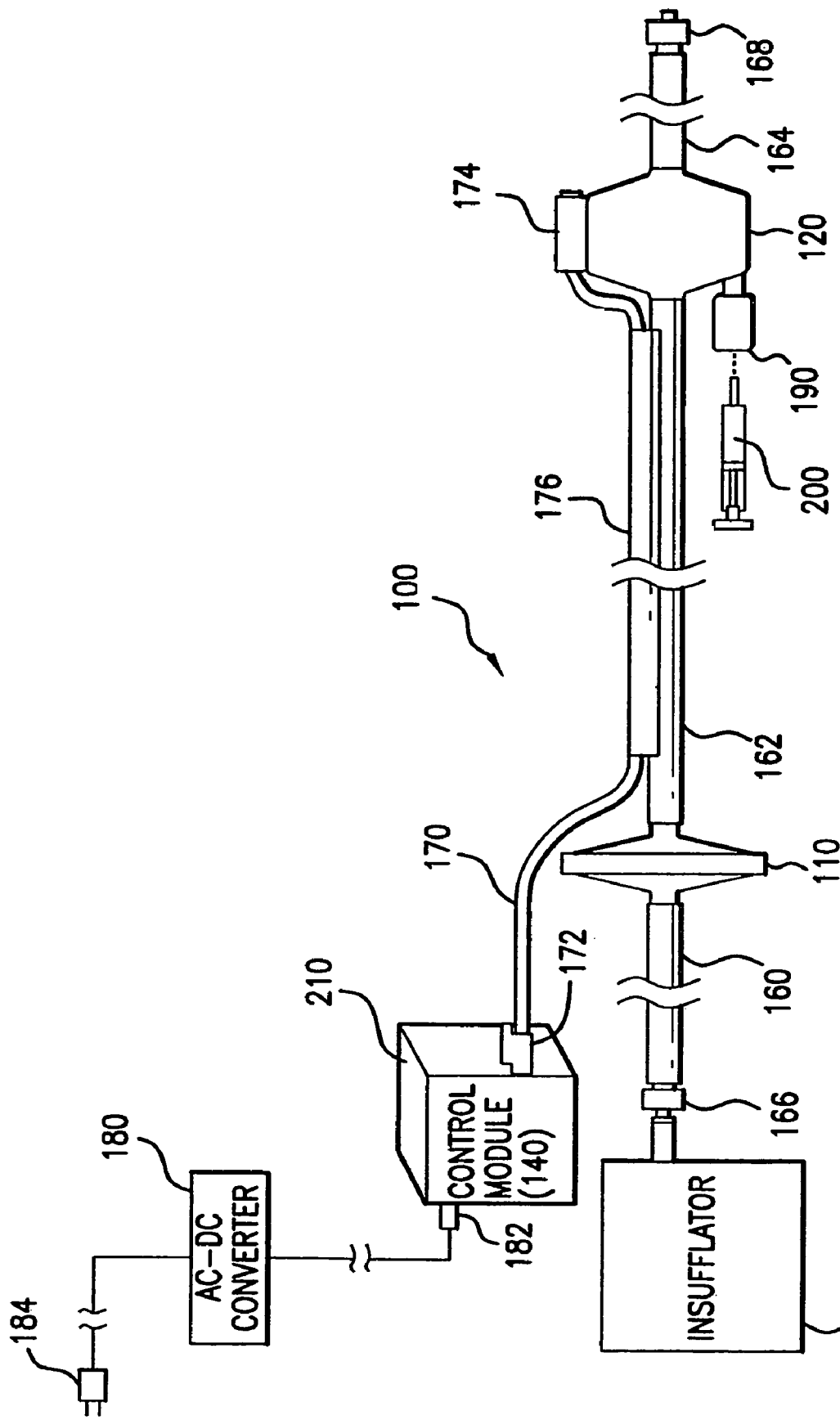
FIG. 1 is a schematic view of an apparatus according to the present invention.

Referring to FIG. 1, the apparatus for treating or conditioning insufflation gas is shown generally at reference numeral 100. The apparatus 100 is adapted to receive gas from a gas source (high or low pressure, high of low flow rate), such as insufflation gas from an insufflator 10 for delivery into a body of a patient. The apparatus comprises a filter 110, a heater/hydrator 120, and a control module 140. A tubing set is provided to connect the various components of the apparatus together. Specifically, a first tube segment 160 connects the outlet of the insufflator 10 to the inlet tubing of the filter 110 via a male Luer lock 166 or any appropriate adapter compatible with the insufflator outlet port. A second tube segment 162 connects the outlet of the filter 110 to the inlet of the heater/hydrator 120. A third tube segment 164 connects the outlet of the heater/hydrator 120 by a male Luer lock 168 (or other appropriate fitting adapter) to a gas delivery device (not shown), such as a trocar, verres needle, endoscope or a tube that enters a body cavity or space that delivers the filtered, heated and humidified gas into the body of a patient. The tubing of the tube segments 160, 162 and 164 is preferably flexible and sufficiently long to permit the insufflator 10 and control module 140 to be placed at a convenient distance from a patient undergoing laparoscopic or other surgery or procedure requiring gas distention, while the heater/hydrator 120 is preferably placed immediately adjacent to the patient.

The filter 110 is an optional element and consists of a high efficiency, hydrophobic filter (for example Gelman Sciences Metricel M5PU025) having a pore size preferably small enough to exclude all solid particles and bacterial or fungal agents that may have been generated in a gas supply cylinder or the insufflator 10 (i.e., 0.5 micron or less and preferably about 0.3 micron). A preferable filter is a hydrophobic filter, such as a glass fiber-type filter, e.g., Metrigard (Gelman Sciences or Porous Media Ultraphobic filter DDDF 4700 M02K-GB). Other suitable filters include polysulfone (Supor, HT Tuffrin, Gelman Sciences) and mixed cellulose esters (GN-6 Metricel, Gelman Sciences), for example. Decreasing the pore size of filter 110 below 0.3 micron causes a concomitant increase in pressure drop of gas, and thus flow rate is reduced significantly. If the medical procedure to be performed requires a relatively high pressure and/or flow rate of gas to the patient, such as laparoscopy, the pore size should preferably not decrease below 0.3 micron. A hydrophobic filter is preferable to a hydrophilic one, as a hydrophobic filter is less likely to tear under water pressure caused by accidentally suctioning or siphoning peritoneal or irrigation fluids.

In one embodiment, the heater/hydrator 120 is connected immediately adjacent to a gas delivery device so that the gas travels a minimum distance from the outlet of the heater/hydrator 120 to the conduit or connection to the interior of a patient. The purpose of this arrangement is to allow gas to be delivered to the patient while still at a temperature and water content sufficiently close to the physiological interior body temperature. That is, the apparatus according to the invention prevents thermodynamic cooling of medical gases in transit to the patient, because it provides a highly efficient heating and humidifying chamber that, as a result of its efficiency, can be quite compact and thus be positioned very near to the patient.

The control module 140 is contained within an electrical housing 210 and is connected to the heater/hydrator 120 by several wire pairs contained within an insulated electrical cable 170. In particular, the cable 170 has a connector 172 at one end that electrically connects into a receptacle of the housing 210 for the control module 140, and at the other end it is electrically connected to the heater/hydrator 120 by a sealed electrical feedthrough 174. The cable 170 is attached to the tube segment 162 by a plastic tape or clip 176. Alternatively, the cable 170 is attached to the tube segment 162 by heat seal, extrusion, ultrasonic welding, glue or is passed through the interior of tube segment 162.

The control module 140 and associated components in the heater/hydrator 120 are preferably powered by an AC-DC converter 180. The AC-DC converter 180 has an output that is connected by a plug connector 182 into a receptacle of the housing 210 to the control module 140, and has a standard AC wall outlet plug 184 that can be plugged into standard AC power outlets. For example, the AC-DC converter 180 is plugged into an AC power strip that is provided on other equipment in an operating room. Alternatively, electrical power for the apparatus is provided by a battery or photovoltaic source. Another alternative is to provide circuitry in the control module 140 that operates on AC signals, as opposed to DC signals, in which case the control module 140 could be powered directly by an AC outlet.

The heater/hydrator 120 has a charging port 190 that is capable of receiving a supply of liquid therethrough to charge the humidification means (described hereinafter) with liquid. For example, a syringe 200 containing a predetermined volume of liquid is introduced into the charging port 190 to inject liquid into the heater/hydrator 120 for an initial charge or re-charge of liquid. The apparatus 100 may be sold with the heater/hydrator 120 pre-charged with a supply of liquid such that an initial charge is not required for operation.

Figure 2:
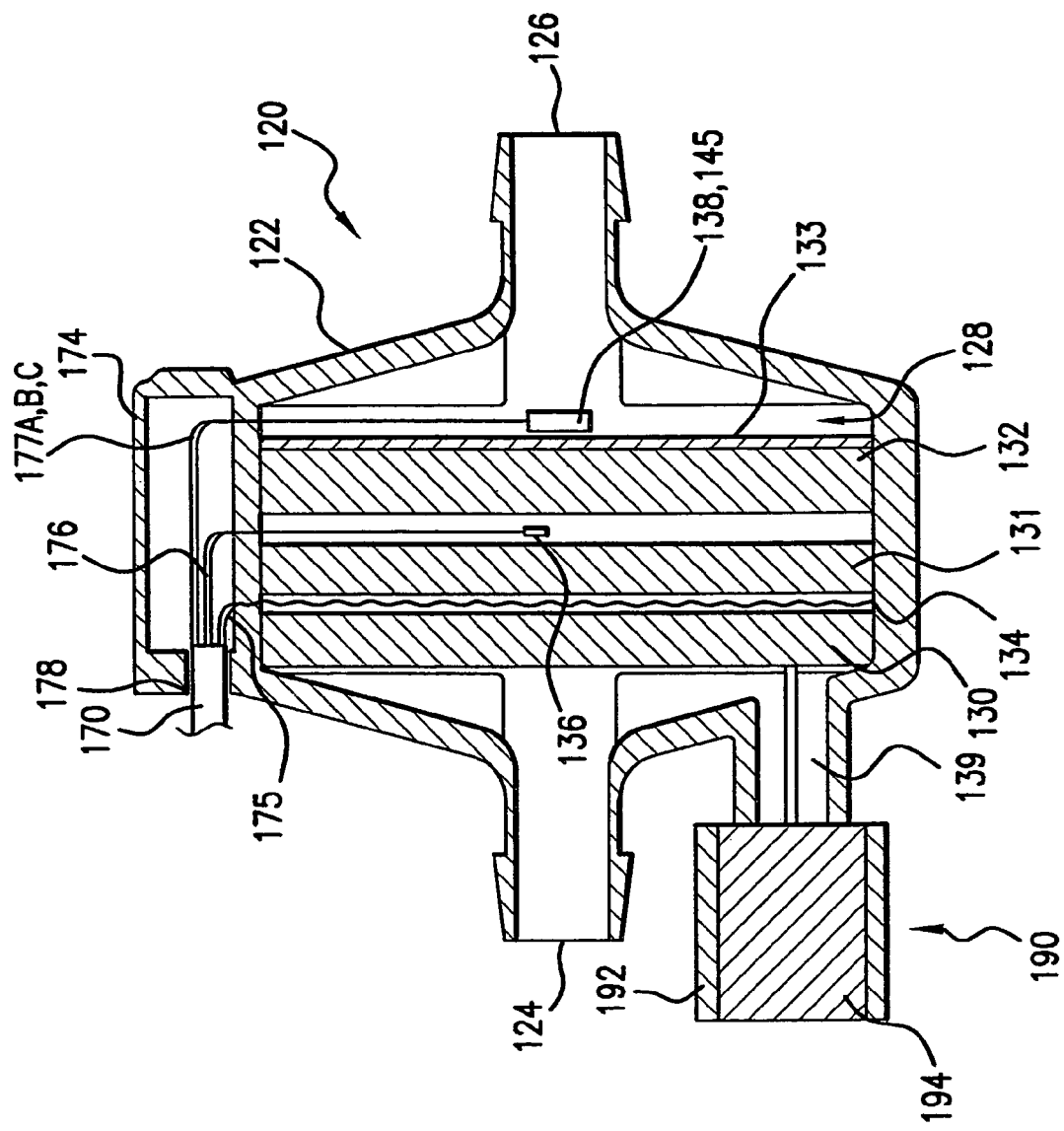
FIG. 2 is a cross-sectional view of the heater/hydrator of the apparatus according to the present invention.

Turning to FIG. 2, the heater/hydrator 120 will be described in greater detail. The heater/hydrator 120 comprises a housing 122 having an (entry port) inlet 124 and an (exit port) outlet 126. The housing 122 defines a chamber 128 that contains elements for substantially simultaneously heating and hydrating (humidifying) the gas supplied through the inlet 124, as well as means for sensing the temperature of the gas and the relative humidity of the gas as it exits the chamber 128.

Specifically, within the chamber 128, there is provided humidification means preferably comprised of one or more layers of liquid-retaining or absorbing padding or sponge material, shown at reference numerals 130, 131 and 132. It should be understood that the number, spacing and absorbency of the liquid-retaining layers 130, 131 and 132 may be varied according to specific applications. Three liquid-retaining layers are shown as an example. The material of the liquid-retaining layers 130, 131 and 132 can be any desirable liquid-retaining material, such as a borosilicate-type material (e.g., a rayon/polyester formed fabric, called NU GAUZE™, manufactured and sold by Johnson & Johnson Medical, Inc.). The pore size of the selected material should be chosen according to a balance of water retention capabilities and low pressure drop considerations. The larger the pore size, the greater the water retention capability for humidification.

Other forms of the humidification means may consist of a chamber of liquid (without liquid-retaining layers) having semi-permeable membrane on opposite ends to allow gas to pass therethrough. The liquid in the chamber could be heated by a heating jacket placed around the chamber to thereby heat and humidify the gas passed therethrough.

The heating means in the heater/hydrator 120 consists of at least one heating element 134 positioned in the housing (substantially) co-located with the humidification means, such as between the liquid-retaining layers 130 and 131. The heating element 134 is an electrically resistive wire, for example, and is described in more detail hereinafter in conjunction with FIG. 3. The heating element 134 is positioned within the humidification means insofar as it is placed preferably between liquid-retaining layers. The heating element 134 heats the insufflation gas supplied through the inlet, under control of a heat control signal supplied by the control module 140, substantially simultaneous with the humidification of the gas as the gas passes through the chamber 128. Additional heating elements may be disposed within the chamber.

In order to sense the temperature and humidity of the gas as it exits the heater/hydrator 120, a temperature sensor 136 and a relative humidity sensor 138 are provided. The temperature sensor 136 may be provided anywhere within the flow of gas in the chamber 128, but is preferably positioned on the downstream side of the heating element 134 between liquid-retaining layers. The temperature sensor 136 is a thermistor (for example, Thermometrics Series BR23, Thermometrics, Inc., Edison, N.J.). It is preferable that the temperature sensor 136 be accurate to within about 0.2° C. In the present invention, the temperature of the gas is preferably sensed after the gas has been humidified so that any change in the temperature of the gas as it is humidified is corrected at that point in the apparatus, thereby compensating for enthalpy changes.

The humidity sensor 138 is positioned in the flow path of gas exiting the chamber 128, preferably downstream from the heating element 134 either between liquid-retaining layers or on the downstream side of the liquid-retaining layers, proximate the exit port 126 of the housing 122. The humidity sensor 138 is preferably not in contact with a liquid-retaining layer. FIG. 2 shows the humidity sensor 138 distal to the liquid-retaining layers, separated from the liquid-retaining layer 132 by a porous mesh (plastic or metal) layer 133 that extends across the interior of the housing 122. The humidity sensor 138 actually is generally not in contact the porous mesh layer 133, but is spaced therefrom as well. The humidity sensor 138 is a humidity-sensitive capacitor sensor, such as a capacitive humidity sensor manufactured by Philips Corporation, which changes capacitance in response to humidity changes. The humidity sensor 138 measures the relative humidity of the gas as it passes through the chamber 128 to enable monitoring of the gas humidity, and in order to provide an indication of the amount of liquid remaining in the humidification means, i.e., in liquid-retainer layers 130, 131 and 132. As will be explained hereinafter, a timer/divider integrated circuit (IC) 145 (FIG. 5), is connected to the humidity sensor 138 and is preferably disposed within the housing 122 together and substantially co-located with the humidity sensor 138.

Electrical connections to the components inside the housing 122 of the heater/hydrator 120 are as follows. A ground or reference lead (not specifically shown) is provided that is connected to each of the temperature sensor 136, heating element 134 and humidity sensor 138 timer/divider 145. A wire 175 (for a positive lead) electrically connects to the heating element 134 and a wire 176 (for a positive lead) electrically connects to the temperature sensor 136. In addition, three wires 177A, 177B and 177C (shown in more detail in FIG. 5) electrically connect to the humidity sensor 138 timer/divider circuitry, wherein wire 177A carries a DC voltage to the timer/divider 145, wire 177B carries an enable signal to the timer/divider 145, and wire 177C carries an output signal (data) from the timer/divider 145. All of the wires are fed from the insulated cable 170 into the feedthrough 174 and through small holes in the housing 122 into the chamber 128. The feedthrough 174 is sealed at the opening 178 around the cable 170. The charging port 190 is attached to a lateral extension 139 of the housing 122. The charging port 190 comprises a cylindrical body 192 containing a resealable member 194. The resealable member 194 permits a syringe or similar device to be inserted therethrough, but seals around the exterior of the syringe tip. This allows a volume of liquid (sterile water, etc.) to be delivered into the chamber 128 without releasing the liquid already contained therein. The resealable member 194 is, for example, Baxter InterLink™ injection site 2N3379. Alternatively, the charging port may be embodied by a one-way valve, a sealable port, a screw cap, a cap with a slit to permit the introduction of a syringe or other device, such as a Safeline™ injection site, part number NF9100, manufactured by B. Braun Medical Inc., or any other covering material or member capable of permitting the introduction of a syringe and preventing the backflow of contained liquid or gas. The chamber 128 will contain approximately 3 to 8 cubic centimeters (cc) (but possibly as much as 10 cc) of liquid, and it is desirable that the gas have a dwell time within the chamber of at least approximately 0.01 to 1.0 sec. A liquid volume of 8 cc in the chamber 128 will usually be adequate for conditioning approximately 180 liters of insufflation gas at a desirable relative humidity of 80-95%. The control module 140, however, will issue a warning when the humidity of the gas being treated by the heater/hydrator 120 drops below a predetermined relative humidity, as explained hereinafter.

The housing 122 preferably has a length to width ratio of about 1:2 to about 1:10, with a more preferable ratio of about 1:3 to about 1:4. Typically, the length of the housing 122 is from about 0.5 cm to about 1.5 cm, and the diameter can be about 3.0 cm to about 5.0 cm. For example, a preferable housing 122 is approximately 3.5 centimeters (cm) in diameter and 1.0 cm thick. The length and width of chamber 128 can be varied such that proper heating and humidification occur. An elongated housing configuration would permit the heater/hydrator 120 to be less intrusive to the medical attendant or surgeon and also be freely movable with respect to other equipment in or around the apparatus 100.

The desirable width and diameter of the chamber is also dependent upon the rate of gas flow from insufflator 10, which is usually from about 1-10 liters/minute, and upon the pressure desired to be maintained, which is affected more by the diameter of chamber 128 than by its length. A person of ordinary skill in the art, given the teachings and examples herein, can readily determine suitable dimensions for chamber 128 without undue experimentation. It should also be noted, however, that upon activating the apparatus or changing the demand on the apparatus (e.g., flow rate or pressure), there is a lag time of only several tenths seconds for sensing the temperature of gas and adjusting the heating element to achieve the proper gas temperature. Such a fast start-up time is extremely beneficial.

Figure 3:
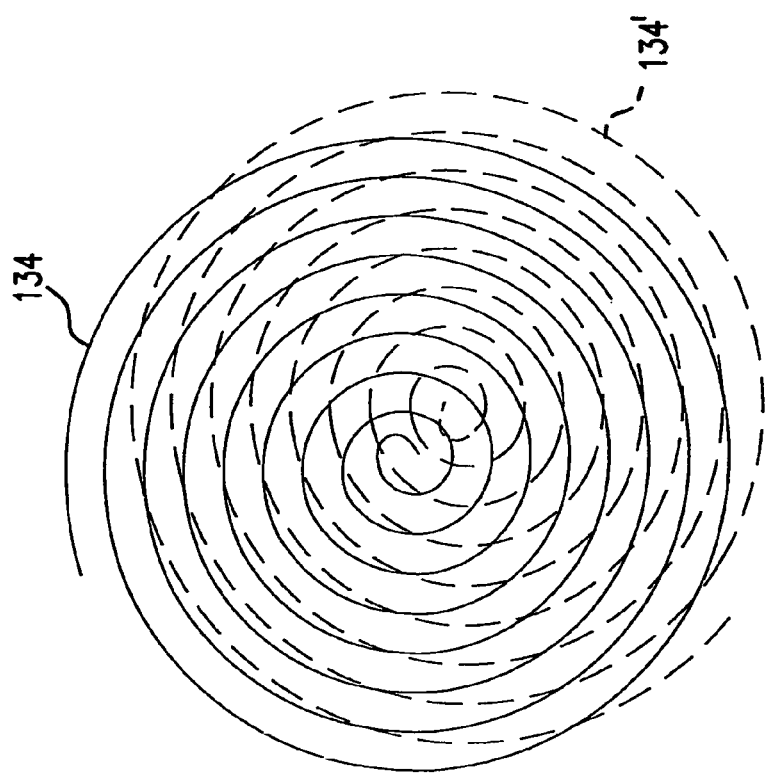
FIG. 3 is a schematic diagram of a heating element used in the heater/hydrator.

Referring to FIG. 3, the heating element 134 is shown in more detail. The heating element 134 is an electrically resistive wire that is disposed in the housing 128 in a concentrical coil configuration having a predetermined number of turns, such as 6-8 turns. Alternatively, a second heating element 134' is provided that is arranged with respect to the heating element 134 such that its coils are offset from those of the first heating element, relative to the direction of gas flow through the chamber. If two or more heating elements are employed, they are preferably spaced from each other in the chamber of the heater/hydrator by approximately 3-4 mm. The first and second heating elements 134 and 134' can be coiled in opposite directions relative to each other. This arrangement allows for maximum contact of the gas flowing through the chamber with a heating element. Other non-coiled configurations of the heating element 134 are also suitable.

Figure 4:
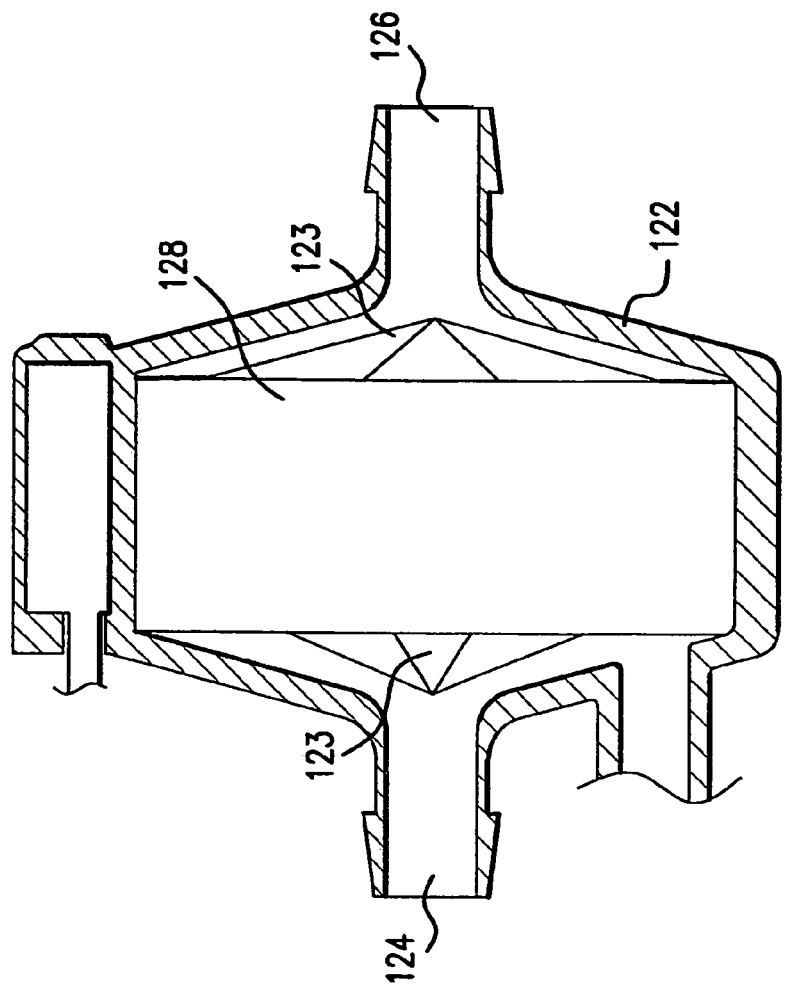
FIG. 4 is a cross-sectional view of the heater/hydrator chamber and showing the fluted gas inlet and outlet of the chamber.

Turning to FIG. 4, another feature of the heater/hydrator 120 is illustrated. At the inlet and/or outlet of the housing 122, fluted surfaces 123 may be provided to facilitate complete dispersion of gas as it is supplied to the heater/hydrator 120. This improves the fluid dynamics of the gas flow through the chamber 128 to ensure that the gas is uniformly heated and humidified as it flows through the chamber 128.

Figure 5:
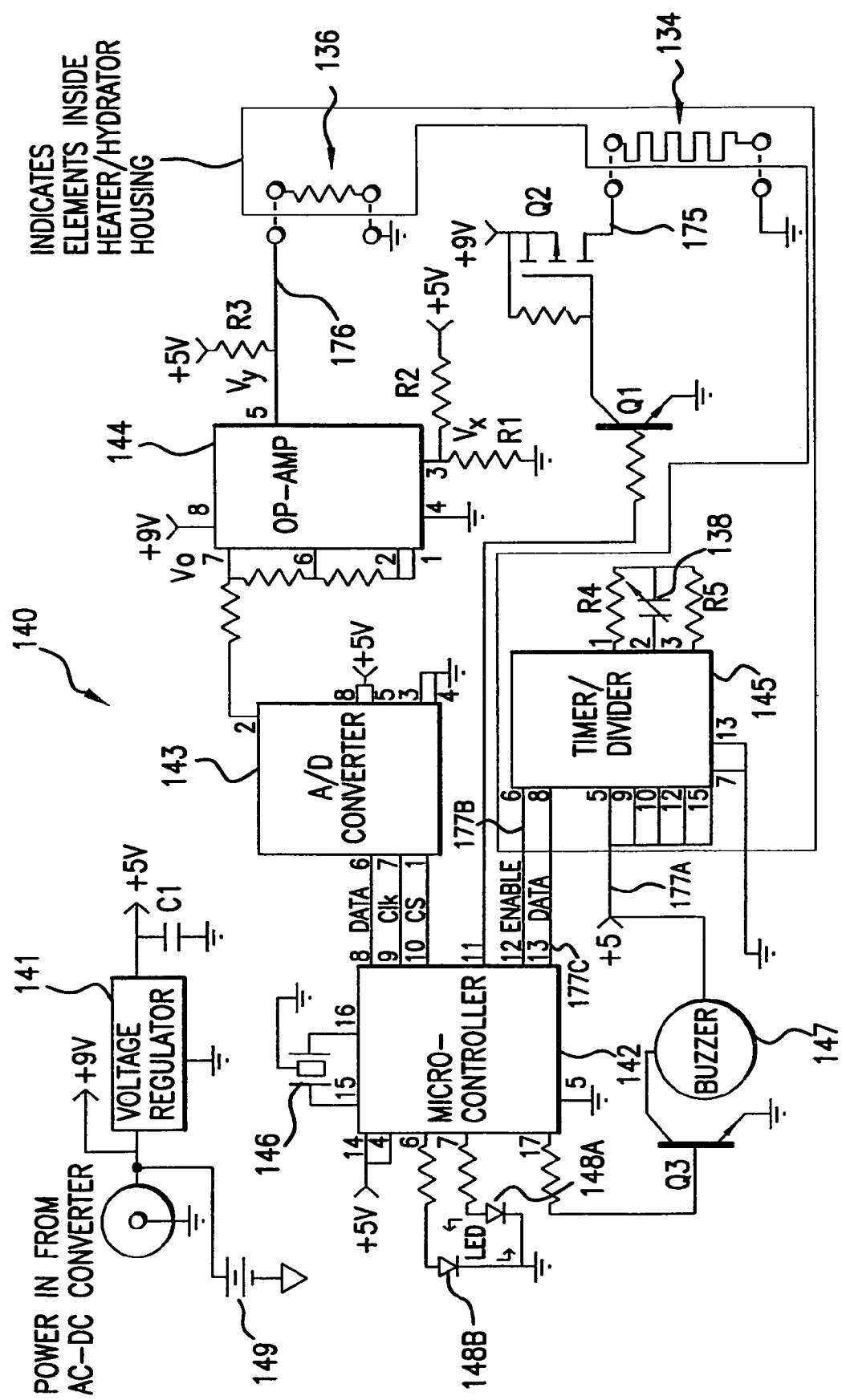
FIG. 5 is a schematic diagram showing the control circuit for controlling the temperature of the gas and for detecting when the humidity of gas is below a predetermined humidity level.

Referring to FIG. 5, the control module 140 will be described in detail. The control module 140 contains monitoring circuitry and control circuitry for the apparatus 100, and comprises a voltage regulator 141, a microcontroller 142, an A/D converter 143, a dual operational amplifier (hereinafter "op-amp") module 144, and a timer/divider 145. The monitoring circuit portion of the control module 140 consists of the combination of the microcontroller 142 and timer/divider 145. The control circuit portion of the control module 140 consists of the microcontroller 142, A/D converter 143 and op-amp module 144. The monitoring circuit monitors the relative humidity of gas exiting the chamber based on a signal generated by the timer/divider 145. The control circuit monitors the temperature of the gas exiting the chamber and in response, controls electrical power to the heating element to regulate the temperature of the gas to a predetermined temperature. While the temperature of the gas exiting the chamber is actively controlled, the relative humidity of the gas in the chamber is not actively controlled; rather it is monitored and an alert is generated when it drops below a predetermined threshold so that appropriate action can be taken, such as replenishing the heater/hydrator with liquid.

FIG. 5 shows that several components are preferably located within the electrical housing 210 (FIG. 1), whereas other components are located within the housing of the heater/hydrator 120 (FIG. 2). In particular, the timer/divider 145 and the associated resistors R4 and R5, are preferably located inside the housing 122 of the heater/hydrator 120, together with the humidity sensor 138 in a circuit package that includes the humidity sensor 138 exposed on one or more surfaces thereof. More specifically, the timer/divider 145 is co-located with humidity sensor 138. This configuration minimizes timing error by stray wiring inductance and capacitance (sensor kept close to active circuits of timer/divider 145). In addition, by co-locating the timer/divider 145 and humidity sensor 138, the need for interconnecting wires is eliminated, thereby avoiding undesirable signal radiation.

The voltage regulator 141 receives as input the DC output of the AC-DC converter 180 (FIG. 1), such as for example, 9V DC, that is suitable for use by the analog components of the control module. The voltage regulator 141 regulates this voltage to generate a lower voltage, such as 5V DC, for use by the digital components of the control module. The capacitor C1 at the output of the voltage regulator 141 serves to filter out any AC components, as is well known in the art. Alternatively, a suitable DC voltage is provided by a battery or photovoltaic source shown at reference numeral 149.

The microcontroller 142 is a PIC16C84 integrated circuit microcontroller that controls system operation. A ceramic resonator 146 (4 MHz) is provided to supply a raw clock signal to pins 15 and 16 of the microcontroller 142, which uses it to generate a clock signal for the signal processing functions explained hereinafter.

The op-amp 144 module is coupled (by wire 176) to the temperature sensor 136 (thermistor) mounted in the housing of the heater/hydrator. The op-amp module 144 is, for example, a LTC1013 dual low-input-offset voltage operational amplifier integrated circuit that includes two op-amps, referred to hereinafter as op-amp A and op-amp B. The non-inverting input of the op-amp A of the op-amp module 144 is pin 3, and pin 2 is the inverting input. The output of op-amp A is pin 1. Op-amp A of the op-amp module 144 is used to buffer the output voltage of the voltage divider formed by resistors R1 and R2. The buffered output voltage, referred to as Vx in FIG. 5, is applied to op-amp B in the op-amp module 144. Op-amp B is configured as a non-inverting-with-offset amplifier with a gain of 21.5, and also receives as input the output of the temperature sensor 136, adjusted by resistor R3, shown as voltage Vy in the diagram. The output voltage of op-amp B is at pin 7, referred to as Vo in FIG. 5. The output voltage Vo is equal to 21.5 Vy−20.5 Vx, which is inversely proportional to the gas temperature in the housing of the heater/dehydrator. The output voltage Vo ranges between 0-5V DC, depending on the temperature of the gas in the chamber.

The A/D converter 143 is an ADC 0831 integrated circuit analog-to-digital converter that receives as input at pin 2, the output Vo of the op-amp module 144. The A/D converter 143 generates a multi-bit digital word, consisting of 8 bits, for example, that represents the output voltage Vo, and is supplied as output at pin 6, which in turn is coupled to I/O pin 8 of the microcontroller 142. The microcontroller 142 commands the A/D converter 143 to output the digital word by issuing a control signal on I/O pin 10 which is coupled to the chip select pin 1 of the A/D converter 143. Moreover, the microcontroller 142 controls the rate at which the A/D converter 143 outputs the digital word by supplying a sequence of pulses on pin 9 applied to clock input pin 7 of the A/D converter 143. The "unbalanced bridge" values of resistors R1, R2 and R3 are chosen to produce a 0-5V DC output over gas temperatures from approximately 20° C. to approximately 45° C. Since the bridge and the reference for the A/D converter 143 are provided by the same 5V DC source, error due to any reference voltage shift is eliminated.

The timer/divider 145 is, for example, a MC14541 precision timer/divider integrated circuit. The humidity sensor 138 is connected to pin 2 and to resistors R4 and R5 as shown. In response to an enable signal output by the microcontroller 142 on pin 12 that is coupled to timer/divider pin 6, the timer/divider 145 generates an output signal that oscillates at a rate determined by the value of the resistor R4, the capacitance of the humidity sensor 138 (which varies according to the relative humidity of the gas inside the heater/hydrator housing) and a predetermined divider constant. For example, the divider constant is 256. Specifically, the output signal of the timer/divider 145 is a square wave oscillating between 0V ("low") and 5V ("high") at a frequency of approximately $1/[256*2.3*R4_t*C_t]$ Hz, where $R4_t$ is, for example, 56 k Ohms, and $C_t$ is the capacitance at some time (t) of the relative humidity sensor 138 depending on the relative humidity of the gas in the chamber. For example, the humidity sensor manufactured by Phillips Electronics, referred to above, can measure between 10-90% RH (relative humidity), where $C_t$ at 43% RH is 122 pF (+/−15%), with a sensitivity of 0.4+/−0.5 pF per 1% RH. The output signal of the timer/divider 145 appears at pin 8, which is coupled to the I/O pin 13 of the microcontroller 142. Thus, the timer/divider 145 is essentially an oscillator circuit connected to the humidity sensor that generates an output signal with a frequency dependent on a capacitance of the humidity sensor. Any oscillator circuit that can generate as output a signal whose frequency is dependent on a variable capacitance may be suitable for the timer/divider 145.

The microcontroller 142 computes a measure of the relative humidity of the gas inside the heater/hydrator housing by timing or measuring a characteristic of the output signal of the timer/divider 145. Specifically, microcontroller measures the time duration of one of the phases of the output signal of the timer/divider 142, such as the "high" phase which is approximately $\frac{1}{2}*[256*2.3*R4_t*C_t]$. This time duration is indicative of the relative humidity of the gas in the chamber of the heater/hydrator since the rate of the oscillation of the timer/divider depends on the capacitance of the humidity sensor 138, as explained above. For example, for a change in RH of 10-50% and/or 50-90%, there is 13% change in the duration of the "high" phase of the timer/divider output signal. The microcontroller 142 monitors the relative humidity of the gas exiting the chamber in this manner and when it drops below a predetermined relative humidity threshold (indicated by a corresponding predetermined change in the oscillation rate of the timer/divider 145), the microcontroller 142 generates a signal on pin 17, called a recharge signal, that drives transistor Q3 to activate an audible alarm device, such as buzzer 147. The buzzer 147 generates an audible sound which indicates that the relative humidity of the gas in the heater/hydrator has dropped below the predetermined threshold and that it is necessary to recharge the heater/hydrator with liquid. The predetermined relative humidity threshold corresponds to a minimum level for a desirable relative humidity range of the gas exiting the heater/hydrator, and may be 40%, for example. The predetermined relative humidity threshold is an adjustable or programmable parameter in the microcontroller 142. Optionally, the microcontroller 142 may generate another warning signal at the output of pin 7 to illuminate a light emitting diode (LED) 148A, thereby providing a visual indication of the humidity dropping below the predetermined relative humidity threshold in the heater/hydrator, and the need to recharge the heater/hydrator 120 with liquid. Further, the microcontroller 142 generates a trouble or warning signal output at pin 6 to drive LED 148B (of a different color than LED 148A, for example) when there is either a "code fault" in the microcontroller 142 (an extremely unlikely occurrence) or when the relative humidity of the gas in the heater/hydrator is les than a critical relative humidity threshold (lower than the predetermined relative humidity threshold), such as 10%. In either case, power to the heating element 134 is terminated in response to the warning signal.

The microcontroller 142 also controls the heating element 134 in order to regulate the temperature of the gas inside the heater/hydrator. Accordingly, the microcontroller 142 processes the digital word supplied by the A/D converter 143 to determine the temperature of the gas inside the heater/hydrator housing. In response, the microcontroller 142 generates a heat control signal on the output pin 11 that drives transistor Q1, which in turn drives the MOSFET power transistor Q2, that supplies current to the heating element 134. The temperature of the gas inside the heater/hydrator is regulated by the microcontroller 142 so that it is within a predetermined temperature range as it exits the heater/hydrator for delivery into the body of a patient. The predetermined temperature range that the gas is regulated to is approximately 35° to 40° C., but preferably is 37° C. As mentioned, above, when the relative humidity inside the heater/hydrator falls below a critical threshold as determined by the monitoring circuit portion of the control module 140, the control circuit portion in response terminates power to the heating element 134 to prevent the delivery of warm gas that is extremely dry.

The circuitry for monitoring the relative humidity of the gas can be embodied by other circuitry well known in the art. In addition, while the control module 140 has been described as having a single microcontroller 142 for monitoring signals representing temperature and relative humidity of the gas exiting the chamber, and for controlling the heating element to control the temperature of the gas, it should be understood that two or more microcontrollers could be used dedicated to the individual functions. In addition, the functions of the microcontroller 142 could be achieved by other circuits, such as an application specific integrated circuit (ASIC), digital logic circuits, a microprocessor, or a digital signal processor.

The volume of gas that can be conditioned with a full supply of liquid in the heater/hydrator depends on the flow rate and pressure used during a procedure. Moreover, the apparatus may be designed to accommodate different anticipated needs for particular procedures. As an example, the chamber of the heater/hydrator is designed to hold 8 to 10 cc of liquid that can humidify 180 liters of gas at a relative humidity level of 80% or more. The microcontroller 142 is programmable to issue the recharge signal when the humidity of the gas drops below the predetermined relativity humidity threshold, independent of the flow rate or pressure of the insufflation gas supply. Preferably, the predetermined relativity humidity threshold is set so that brief periods of high pressure or high flow rate do not cause this threshold to be triggered, because the humidity level will return to greater-than-threshold levels shortly after the high pressure/flow rate periods ends.

With reference to FIGS. 1 and 2, the setup and operation of the apparatus 100 will be described. The AC/DC converter 180 is plugged into an 110V AC power source, such as a wall outlet or a power strip. The control module 140 is connected to the AC/DC converter 180. Alternatively, the apparatus 100 may be powered by a battery or photovoltaic source. The heater/hydrator tubing set is then installed by attaching one end of the tube segment 160 to the outlet of the insulator 10 by the Luer lock 166. The tube segments 160, 162 and 164 may be pre-attached to the filter 110 and the heater/hydrator 120 for commercial distribution of the apparatus 100. The cable 170 is installed into the electrical housing 210 of control module 140 by the connector 172. The heater/hydrator 120 is charged with a supply of liquid by the syringe 200. For example, 8 cc of liquid, such as sterile water, is drawn into the syringe 200. The syringe 200 is then inserted into the charging port 190 so that a needle or cannula of the syringe 200 penetrates the resealable member 194 (FIG. 2) and the liquid is injected into the heater/hydrator 120 to be absorbed by the liquid-retaining layers. The syringe 200 is then removed from the charging port 190, and the charging port 190 seals itself. The free end of the tube segment 164 is attached to a gas delivery device by the Luer lock 168 or other appropriate connector. Alternatively, the heater/hydrator 120 may be precharged with liquid, thus not requiring a charge prior to operation.

Once the insulator 10 is activated, it receives gas from a gas supply cylinder and regulates the pressure and flow rate of the gas, both of which can be adjusted by the operator. The pressure and volumetric flow rate of the gas, both of which can be adjusted by the operator. The pressure and volumetric flow rate are controlled by adjusting controls (not shown) on the insufflator 10. Insufflator gas then flows through the tube segment 160 into the optional filter 110 where it is filtered, and then through tube segment 162 into the heater/hydrator 120. In the heater/hydrator 120, gas comes into contact with electrical heating element 134 and the humidifying liquid-retaining layer(s) 130-132 which are positioned within the flow path of the gas, as shown in FIG. 2. In chamber 128, insufflator gas is simultaneously heated and humidified to the proper physiological range by regulation of the heating element 134 and liquid content of the liquid-retaining layers 130-132 such that the temperature of gas exiting chamber 128 is within a preselected physiological temperature range (preferably 35° to 40° C., though any desired temperature range can be preselected), and within a preselected range of relative humidity (preferably above 40% relative humidity, such as in the range of 80-95% relative humidity). If the apparatus is operated with the heater/hydrator 120 not charged with liquid either because the user forgot to manually charge it before initiating operation, or the apparatus was sold without a pre-charge of liquid (i.e., in a dry state), the relative humidity of the gas in the chamber of the heater/hydrator 120 will be detected to be below the predetermined threshold and the alarm will be activated, alerting the user that the heater/hydrator 120 requires charging of liquid. The apparatus will automatically issue an alarm to alert a user to the need for charging the heater/hydrator 120 with liquid, thereby avoiding further delivery of unhydrated gas into a patient.

With further reference to FIG. 5, the control module 140 monitors the relative humidity of the gas exiting the chamber and further regulates the temperature of the gas in the chamber 128. In particular, the microcontroller 142 generates a recharge signal when the relative humidity of the gas in the chamber drops below the predetermined relative humidity threshold, indicating that the liquid supply in the heater/hydrator 120 requires replenishing. An audible alarm is issued by the buzzer 147 and/or a visual alarm is issued by LED 148A to warn the medical attendant or user that the heater/hydrator 120 requires recharging. Preferably, the microcontroller 142 continues the alarm until the humidity in the chamber returns to a level above the predetermined relative humidity threshold, which will occur when the heater/hydrator 120 is recharged with liquid. Moreover, the microcontroller 142 will issue a second alarm, such as by energizing LED 148B, when the relative humidity level of gas in the heater/hydrator 120 drops below the critical relative humidity threshold, at which point electrical power to the heating element 134 is terminated. In addition, the microcontroller 142 controls the temperature of the gas by controlling electrical power supplied to the heating element 134.

The apparatus and method according to the present invention provide several advantages over similar devices heretofore known, including those disclosed in commonly assigned U.S. Pat. No. 5,411,474 to Ott, et al.

In particular, the apparatus of the present invention provides for control of the temperature and monitoring of the humidification of the gas, and of particular importance, generates an audible or visual alarm indicating that the heater/hydrator requires recharging of liquid to sustain and provide timed re-supply of liquid in order to maintain a flow of heated/hydrated gas. The alarm is maintained until the heater/hydrator is recharged and the humidity of the gas returns to a predetermined level. In addition, the apparatus disclosed herein is easily installed and prepared for use with a minimal amount of lines and tubes. The rechargeable feature of the heater/hydrator eliminates the need for an additional liquid supply tube connected to the heater/hydrator. If needed, the heater/hydrator may be recharged with liquid several times during a procedure.

In addition, the power supply for the apparatus is derived from a standard AC wall outlet or power strip. Power strips are often provided on medical carts already used in the operating room environment. By using a power supply derived from a (normally) uninterrupted AC source, as opposed to the finite amount of power that can be supplied by a battery, accommodating surgical procedures that last longer than anticipated is not a concern. The control circuitry for the apparatus is preferably contained in an electrical housing that is relatively movable with respect to the remainder of the apparatus, and therefore can be placed in a non-interfering position in the operating room. For example, the electrical housing of the control module can be attached by tape or Velcro to the side of the insufflator or other stable structure in the operating room, and not encumber the remainder of the apparatus of affect parameter settings of the insufflator.

The method and apparatus of this invention can be utilized for many medical procedures requiring the provision of heated and humidified gas. The optional filtration may also be utilized according to the sterility of gas required for the procedure. The gas is chosen according to the procedure to be performed and can be any medically useful gas, such as carbon dioxide, oxygen, nitrous oxide, argon, helium, nitrogen and room air and other inert gases. Preferable gases for endoscopy are carbon dioxide and nitrous oxide. A combination of the above gases can also be used, i.e., 100% of a single gas need not be used. The procedure is preferably endoscopy such as laparoscopy, colonoscopy, gastroscopy, bronchoscopy, and thorascoscopy. However, it may also be utilized for providing heated and humidified oxygen or any anesthetic gases or combination of gases for breathing, for example, or to administer anesthesia or breathing therapy. In particular, the compact size of the apparatus make the invention portable and thus suitable for uses requiring portability. The gas delivery device that provides the direct contact to the patient should be selected according to the medical procedure to be performed as known to those skilled in the art. The gas that is conditioned by the apparatus may be pressure controlled, volumetrically controlled or both.

Throughout this application, various patents publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed:

1. A method of treating gas for endoscopic surgery comprising the steps of:

a) directing a gas from a laparoscopic insufflator into a chamber;
b) humidifying the gas within the chamber with a volume of liquid;
c) sensing the humidity of the gas within the chamber;
d) detecting when the humidity of the gas in the chamber is below a predetermined humidity level; and
f) generating an audio or visual recharge signal when the humidity of the gas in the chamber is below the predetermined humidity level.

2. The method of claim 1, further comprising replenishing the chamber with liquid in response to the recharge signal.

3. The method of claim 2, wherein detecting comprises determining when the relative humidity of the gas in the chamber drops below the predetermined humidity level.

4. The method of claim 2, and further comprising generating an alarm when the humidity of the gas in the chamber is below the predetermined humidity level.

5. The method of claim 4, and further comprising recharging the chamber with liquid in response to the alarm.

6. The method of claim 4, wherein the alarm is continued until the humidity of the gas in the chamber is above the predetermined humidity level.

7. The method of claim 1, and further comprising generating an audio and/or visible alarm when it is determined that the humidity of the gas in the chamber drops below the predetermined humidity level.

8. The method of claim 1, and further comprising heating the gas within the chamber with a heating element, sensing the temperature of the gas within the chamber, and controlling electrical power to the heating element in response to the sensing of the temperature.

9. A method of treating gas for endoscopic surgery comprising the steps of:
a) directing a gas from a laparoscopic insufflator into a chamber;
b) humidifying the gas within the chamber with a volume of liquid;
c) sensing the humidity of the gas within the chamber;
d) detecting when the humidity of the gas in the chamber is below a predetermined humidity level; and
f) generating a recharge signal when the humidity of the gas in the chamber is below the predetermined humidity level, and further comprising heating the gas within the chamber, with a heating element, sensing the temperature of the gas within the chamber, and controlling electrical power to the heating element in response to the sensing of the temperature and terminating electrical power to the heating element when the humidity of the gas in the chamber is below the predetermined humidity level.

10. The method of claim 8, wherein the humidifying and heating are performed on the gas substantially simultaneously within the chamber.

11. The method of claim 8, wherein the sensing of humidity and sensing of temperature are performed in the flow path of the gas downstream from the location of the heating and humidifying in the chamber.

12. The method of claim 1, and further comprising positioning the chamber immediately adjacent the patient.

13. The method of claim 1, and further comprising filtering the gas prior to humidifying the gas.

14. The method of claim 1, and further comprising heating the gas within the chamber with a heating element to a temperature between 35 and 40° C., sensing the temperature of the gas; and controlling electrical power to the heating element so as to keep the temperature of the gas within the chamber in the range of 35 to 40° C.

15. The method of claim 1, further comprising heating the gas within the chamber with a heating element to a physiologic temperature, sensing the temperature of the gas; and controlling electrical power to the heating element so as to keep the temperature of the gas within the chamber at the physiologic temperature.

16. A method of treating gas for endoscopic surgery comprising the steps of:
a) directing a gas from a laparoscopic insufflator into a chamber;
b) heating and humidifying the gas within the chamber;
c) treating the gas by admixing at least one agent, other than air or water, with the gas;
d) sensing at least one of the temperature or humidity of the gas within the chamber; and
e) delivering the treated gas with the admixed agent to the interior of the patient.

17. The method defined in claim 16, further comprising generating a recharge signal when the humidity of the gas is below a predetermined desired level.

18. The method defined in claim 17, wherein the at least one agent is a liquid phase agent.

19. The method defined in claim 17, wherein the at least one agent is a solid phase agent.

20. An apparatus for treating gas prior to the use of the gas in endoscopic surgery, the gas being received into the apparatus from a laparoscopic insufflator, and the gas exiting the apparatus being in flow communication with a means for delivering the gas to the interior of the patient, the apparatus comprising:
a) a housing defining a chamber having an entry port and an exit port, the exit port being in flow communication with the means for delivering the gas to the interior of the patient, and the inlet being in flow communication
b) a source of humidity disposed within the chamber;
c) a humidity sensor disposed within the chamber;
d) monitoring means connected to the humidity sensor for detecting when the relative humidity of the gas in the chamber is below a predetermined relative humidity threshold, and
e) a means for delivering the gas to the interior of the patient connected to the exit pod of the chamber.

21. An apparatus for treating gas prior to the use of the gas in endoscopic surgery, comprising:
a) a housing defining a chamber having an entry port and an exit port;
b) a laparoscopic insufflator connected to the inlet of the chamber;
c) a means for delivering gas to a patient connected to the outlet of the chamber;
d) a source of humidity disposed within the chamber;
e) a humidity sensor disposed within the chamber; and
f) electronic circuitry connected to the humidity sensor to determine when the relative humidity of the gas in the chamber falls below a critical relative humidity threshold.

22. The apparatus defined in claim 21 comprising a heater disposed within the chamber.

23. The apparatus defined in claim 22, comprising a temperature sensor disposed within the chamber.

24. The apparatus defined in claim 23 comprising:
a) a temperature sensor disposed within the chamber; and
b) control circuitry connected to the temperature sensor and to the heater to control electrical power to the heater.

* * * * *